(12) United States Patent  
Schiesser et al.

(10) Patent No.: US 9,895,309 B2  
(45) Date of Patent: Feb. 20, 2018

(54) SELENOSUGARS FOR SKIN TISSUE REPAIR

(71) Applicant: SELENO THERAPEUTICS PTY LTD., Victoria (AU)

(72) Inventors: Carl Herbert Schiesser, Carlton (AU); Corin Storkey, Carlton (AU); Michael Jonathon Davies, Newtown (AU)

(73) Assignee: SELENO THERAPEUTICS PTY LTD., Victoria (AU)

( * ) Notice: Subject to any disclaimer, the term of this patent is extended or adjusted under 35 U.S.C. 154(b) by 0 days.

(21) Appl. No.: 15/517,811

(22) PCT Filed: Oct. 10, 2014

(86) PCT No.: PCT/AU2014/000960  
§ 371 (c)(1),  
(2) Date: Apr. 7, 2017

(87) PCT Pub. No.: WO2016/054671  
PCT Pub. Date: Apr. 14, 2016

(65) Prior Publication Data  
US 2017/0252296 A1    Sep. 7, 2017

(51) Int. Cl.  
*A61K 9/00*    (2006.01)  
*A61K 31/33*    (2006.01)

(52) U.S. Cl.  
CPC ............ *A61K 9/0014* (2013.01); *A61K 31/33* (2013.01)

(58) Field of Classification Search  
CPC .............................. A61K 31/33; A61K 9/0014  
See application file for complete search history.

(56) References Cited

U.S. PATENT DOCUMENTS

2014/0206658 A1*  7/2014  Schiesser ............... A61K 31/33  
514/183

* cited by examiner

*Primary Examiner* — Savitha M Rao  
(74) *Attorney, Agent, or Firm* — Roy Gross; The Roy Gross Law Firm, LLC (57) ABSTRACT

A topical composition for skin repair comprising selenosugars of formula (1): (Formula (I)) wherein, n is 1, 2 or 3; m is 2, 3, 4; or 5; and each R1 is independently-(optionally substituted $C_1$-$C_3$ alkyiene)p-OH, where p is 0 or 1 or a pharmaceutically acceptable salt thereof.

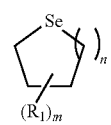

6 Claims, 10 Drawing Sheets

SELENOSUGARS FOR SKIN TISSUE REPAIR

FIELD

The present invention relates to compounds and compositions useful for treatment of damaged living skin tissue and the repair thereof (tissue repair).

In a preferred embodiment the compounds and compositions are based on selenium containing carbohydrate derivatives or selenium containing compounds structurally related to carbohydrates (selenosugars). The invention also relates to the topical use of these selenosugars and compositions comprising at least one selenosugar for promoting tissue repair.

While the present invention will be described with reference to the healing of wounds, it will be readily apparent to the person skilled in the art that the invention is not so limited, but relates to tissue repair generally, with application to numerous conditions that include non-healing chronic wounds.

BACKGROUND

It is to be appreciated that any discussion of documents, devices, acts or knowledge in this specification is included to explain the context of the present invention. Further, the discussion throughout this specification comes about due to the realisation of the inventor and/or the identification of certain related art problems by the inventor. Moreover, any discussion of material such as documents, devices, acts or knowledge in this specification is included to explain the context of the invention in terms of the inventor's knowledge and experience and, accordingly, any such discussion should not be taken as an admission that any of the material forms part of the prior art base or the common general knowledge in the relevant art in Australia, or elsewhere, on or before the priority date of the disclosure and claims herein.

'Wound healing' is a general term for the process by which living skin tissue repairs itself in response to an injury. An injury triggers a complex set of overlapping biochemical events characterised by three main phases; (1) inflammation, (2) proliferation and (3) remodeling.

For example, within a few minutes of an injury to skin, platelets adhere to the injury site, become activated, and aggregate. The biochemical coagulation cascade is activated to form a clot of aggregated platelets enmeshed in cross-linked fibrin protein that stops active bleeding (hemostasis).

During the inflammation phase, neutrophils and macrophages phagocytose bacteria and cell debris, effectively removing them from the wound. During this phase platelet derived growth factors are released into the wound and cause the migration and division of cells during the proliferative phase.

During the proliferation phase, angiogenesis occurs and vascular endothelial cells form new blood vessels. Collagen deposition also occurs along with granular tissue formation, epithelialization, and wound contraction. In fibroplasia and granulation tissue formation, fibroblasts grow and form a new, provisional extracellular matrix by excreting collagen, fibronectin and other materials. Concurrently, re-epithelialization of the epidermis occurs, in which epithelial cells proliferate over the wound bed to cover the new tissue.

The wound contracts as myofibroblasts grip the wound edges and contract. When the cells' roles are complete, many become redundant and undergo apoptosis. During maturation and remodeling, collagen is remodeled and realigned along tension lines, and more redundant cells undergo apoptosis.

Skin tissue repair is thus a complex process and is susceptible to disruption, potentially resulting in the formation of non-healing chronic wounds. Factors that can contribute to non-healing chronic wounds include metabolic syndrome (diabetes, venous or arterial disease), infection, and metabolic deficiencies of old age.

Many different chemical moieties including trace elements such as selenium have been orally, or internally administered to a subject in attempts to improve wound healing. For example attempts have been made to show that selenium salt (in the form of sodium selenite) taken orally can accelerate wound healing in the diabetic condition— allegedly decreasing the expression of connexins and serum glucose in diabetic wounds as compared to non-diabetic wounds. In the diabetic wounds, the low levels of vascular endothelial growth factor and extracellular superoxide dismutase were restored to normal level following selenium administration and angiogenesis improved at the wound site (Baipai S et al, *Biol Trace Elem Res.* 2011 Ded; 144(1-3): 327-38. Epub 2011 Jun. 2). However the lack of rigorous statistical analysis of the results leaves the conclusions open to question. It is however apparent that the results are attributed to the antioxidant characteristic of the selenium salt. Interestingly, the results indicate that oral selenium salt administration appeared ineffective in accelerating wound healing in non-diabetic wounds.

In the past the consumption of selenium in health supplements and sports drinks has been associated with bolstering antioxidant defences and immune health, minimising the adverse effects of free radicals. For example, U.S. Pat. No. 4,668,515 describes a selenium-containing drink to maintain health and prevent the formation of spontaneous tumours of the mammary gland. DE 44 37 403 describes another antioxidant composition including bound selenium, also for internal administration. More specifically these treatments have been based on the antioxidant activity of such compounds.

Selenium compounds such as the water-soluble glutathione peroxidase (GPx) mimic DL-trans-3,4-dihydroxy-1-selenolane ($DHS_{red}$) have been investigated for their potential to heal acute gastric ulcers induced by non-steroidal anti-inflammatory drugs (NSAID's). It is suggested that the healing action of $DHS_{red}$ in conjunction with omeprazole was due to antioxidant activity, ability to protect mucin and augmentation of prostaglandin synthesis. (Chakraborty S et al, Free Radical Research, 2012; 46(11) 1378-1386).

US 2011/0038956 (Kuklinski et al) teaches the use of selenite- or selenate-containing preparations supplemented with pharmaceutically acceptable acids for topical, buccal or mucosal administration to utilise the anti-oxidant activity of selenium to treat skin conditions caused by papillomavirus or mycoses and periodontal diseases such as stomatitis, aphthae or leucoplakia.

The use of the anti-oxidant activity of selenium containing compounds and their solubility in aqueous solutions such as plasma, is also taught and disclosed in WO 2012 054988 (U.S. Ser. No. 13/881,594). WO 2012/054988 identifies a group of seleno-compounds that regulate the presence of reactive oxygen species (ROS), such as hypohalous acids (e.g., HOCl and HOBr) and/or to minimise the adverse impact of such ROS by inhibiting or minimising the pathogenesis of certain conditions or disease states which are linked to tissue damage by ROS. More specifically the compounds comprise a stable seleno-moiety, which acts as a radical scavenger and in particular a scavenger of ROS or free-radicals derived from non-radical ROS and as such these compounds are able to function as antioxidants. Such compounds have significant potential in treating disorders linked to the effect of free radicals such as atherosclerosis, cystic fibrosis, sepsis, rheumatoid arthritis and other inflammatory disorders, some cancers, asthma, and cardiovascular diseases.

SUMMARY OF THE INVENTION

An object of the present invention is to improve skin tissue repair, particularly in relation to wound healing, including the healing of chronic wounds.

A further object of the present invention is to alleviate at least one disadvantage associated with the related art.

It is an object of the embodiments described herein to overcome or alleviate at least one of the above noted drawbacks of related art systems or to at least provide a useful alternative to related art systems.

In a first aspect of embodiments described herein there is provided a topical composition comprising selenosugars of formula (I):

Formula (I)

wherein,
n is 1, 2 or 3;
m is 2, 3, 4; or 5; and
each R1 is independently-(optionally substituted $C_1$-$C_3$ alkylene)p-OH, where p is 0 or 1.

The selenium-containing compounds of formula (1) are typically derived from or related to common carbohydrates. Where used herein the terms 'selenosugars' or 'selenium-containing carbohydrates' refer to compounds of the type defined by Formula (I). In a particularly preferred embodiment of the present invention the compounds of formula (I) are derived from pentose, hexose and heptose sugars.

In a further aspect of the invention there is provided a method for improving skin tissue repair including wound healing comprising the topical administration of a selenosugar of formula (I), or a pharmaceutically acceptable salt thereof, or a composition comprising a selenosugar of formula (I), or a pharmaceutically acceptable salt thereof.

Without wishing to be bound by theory it is thought that the selenosugars of the present invention have effect on one or more of endothelial cells, neutrophils, macrophages, keratinocytes and fibroblasts involved in the repair of skin, such as in the wound healing process. More particularly it is believed that selenosugars increase activity such as angiogenesis and neo-vascularisation associated with endothelial cells, the removal of bacteria and cell debris by neutrophils and macrophages, and the activity of keratinocytes and fibroblasts during re-epithelialisation, formation of new connective tissue and tissue remodeling.

In another aspect the invention provides the use of a selenosugar of formula (I), or a pharmaceutically acceptable salt thereof, in the manufacture of a medicament for use in skin tissue repair including wound healing treatment.

In a preferred aspect the invention provides the use of a selenosugar of formula (I), or a salt thereof, for use in skin tissue repair including wound healing.

In a further aspect the skin tissue repair is directed to a non-healing chronic wound associated with a disease or other physiological state. In a particular embodiment the non-healing chronic wound is associated with metabolic syndrome, infection, or metabolic deficiencies of old age.

In a further aspect the invention provides a method of protecting against non-repair of tissue, said method comprising the step of administering to a subject a selenosugar compound of formula (I) or a pharmaceutically acceptable salt thereof.

In a further aspect of the invention there is provided a pharmaceutical composition for use in tissue repair, the composition comprising an effective amount of a selenosugar of formula (I), or a pharmaceutically acceptable salt thereof and optionally a carrier or diluent.

Other aspects and preferred forms are disclosed in the specification and/or defined in the appended claims, forming a part of the description of the invention.

In essence, embodiments of the present invention stem from the realization that certain selenosugars have a surprising effect on one or more of the pathways involved in tissue repair. For example selenosugars have the hitherto unexpected effect of increasing neutrophil migration into a wound, but not macrophage migration.

Advantages provided by the present invention with respect to wound healing comprise the following:
reduced inflammation,
improved vascularisation,
increased rate of healing,
reduced scaring/improved remodeling.

Further scope of applicability of embodiments of the present invention will become apparent from the detailed description given hereinafter. However, it should be understood that the detailed description and specific examples, while indicating preferred embodiments of the invention, are given by way of illustration only, since various changes and modifications within the spirit and scope of the disclosure herein will become apparent to those skilled in the art from this detailed description.

BRIEF DESCRIPTION OF THE DRAWINGS

Further disclosure, objects, advantages and aspects of preferred and other embodiments of the present application may be better understood by those skilled in the relevant art by reference to the following description of embodiments taken in conjunction with the accompanying drawings, which are given by way of illustration only, and thus are not limitative of the disclosure herein.

The drawings illustrate the following:

FIG. 3 relates to % neutrophils;

FIG. 4 relates to % interleukin-6 (IL-6);

FIG. 5 relates to % actin;

FIG. 8 relates to % elastin;

FIG. 7 relates to % caspase 3 protein;

FIG. 8 relates to % F4/80 (a mouse macrophage-specific membrane marker);

FIG. 9 relates to % monocyte chemotactic protein-1 (MCP-1);

FIG. 10 relates to % myeloperoxidase (MPO);

FIG. 11 relates to % vascular endothelial growth factor (VEGF);

FIG. 12 relates to % von Willebrand factor (vWF) a blood glycoprotein involved in halting the escape of blood from vessels following vascular injury;

FIG. 15 is a plot illustrating the performance of a selenosugar according to the present invention (1,4-anhydro-4-seleno-D-talitol) (8) against a similar water-soluble selenium compound that is not sugar derived ($DHS_{red}$) (10) in non-diabetic (wt) mice over time.

EXPERIMENTAL RESULTS

The selenosugars of the present invention have been experimentally tested by topical application to wounds exhibited in a normal (wildtype) mouse model, a diabetic (db/db) mouse model, and compared with a non-treated control.

In the experimental testing according to the present invention, pairs of circular incision wounds on the backs of wildtype C57/BL6 and db⁻/db⁻ mice (n=12 each) were treated daily with a selenosugar according to the current invention or vehicle, topically for 10 days. Wound closure, vascular perfusion and tissue histology were assessed.

Wound closure in wildtype mice treated with selenosugar was 2-fold greater than controls at day 4 (32% vs 17.5%, p<0.05) and greater at day 10 (82% vs 65%, p<0.01).

Again, without wishing to be bound by theory it is hypothesised that the observed results reflect the actions of the selenosugars on one or more of the three groups of cells—(i) endothelial cells, (ii) neutrophils and macrophages, and (iii) keratinocytes and fibroblasts—and the parts of the wound healing process with which they are associated.

For instance, the observed reduction in MCP1—a member of the small inducible gene (SIG) family, that plays a role in the recruitment of monocytes to the site of a wound. This likely contributes to more rapid wound healing.

Figure 4A:
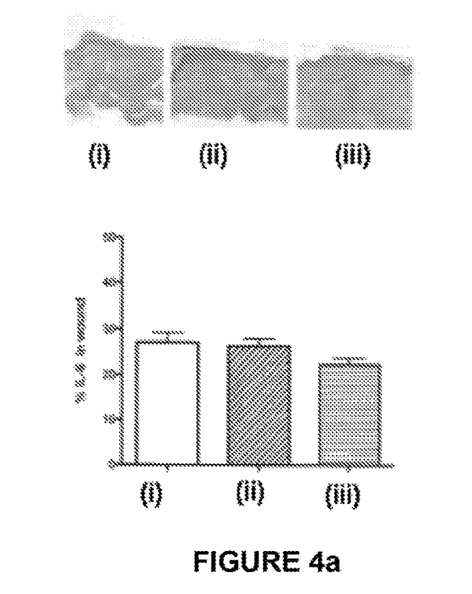
Figure 4B:
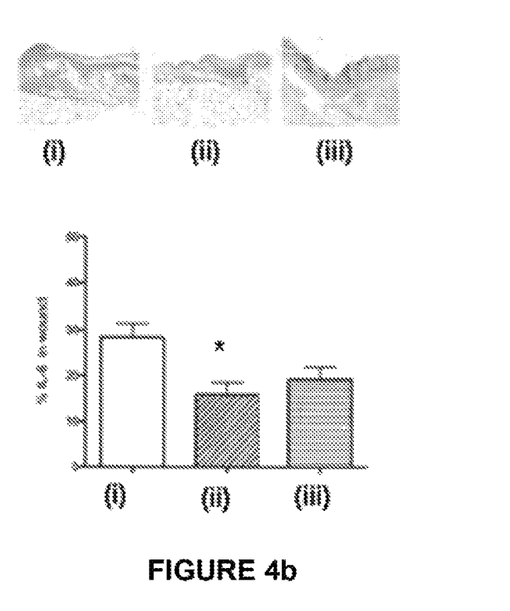
Figure 5A:
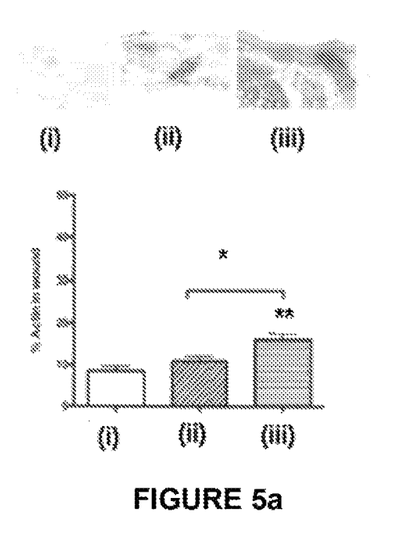
Figure 5B:
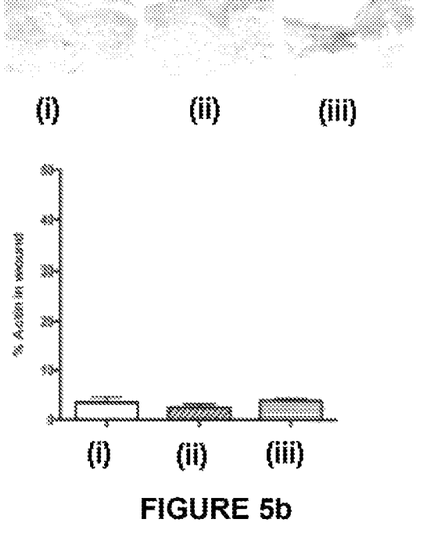

The observed results also include increased neutrophil migration into areas undergoing repair, but no concomitant increase in macrophage or build up of MPO in wounds. In some wounds, a reduction in IL-6 (FIG. 4) is apparent, particularly in wounds associated with diabetic mice.

Figure 6A:
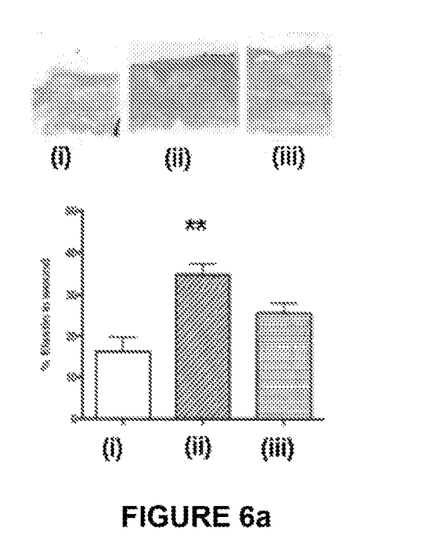
Figure 6B:
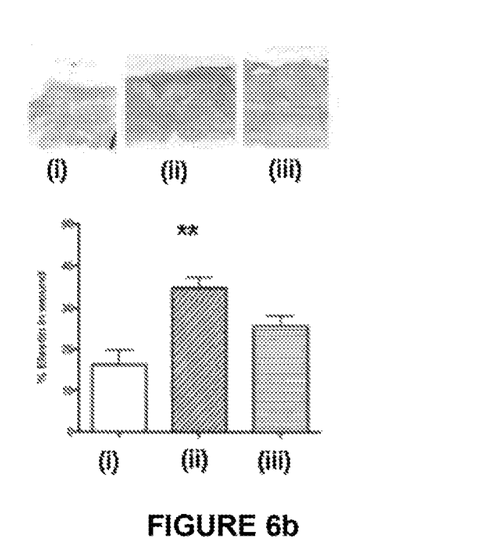
Figure 7A:
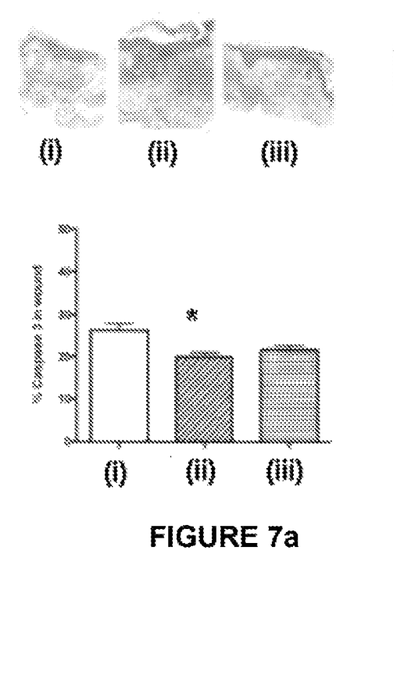
Figure 7B:
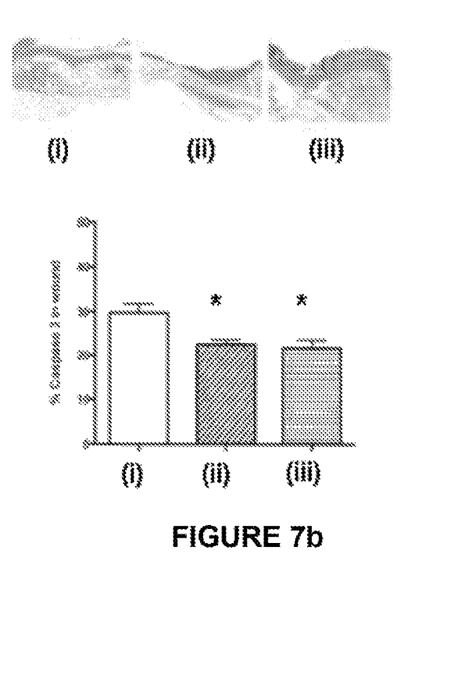
Figure 8A:
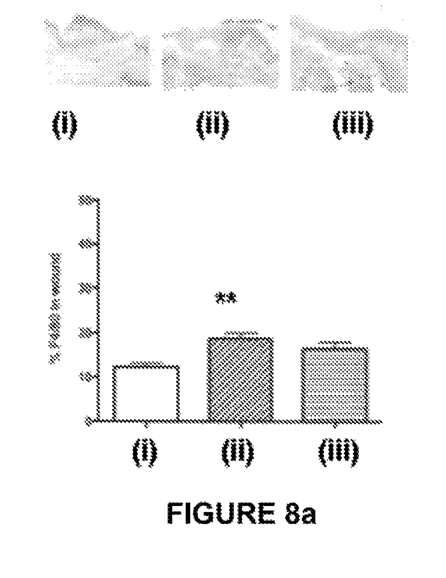
Figure 8B:
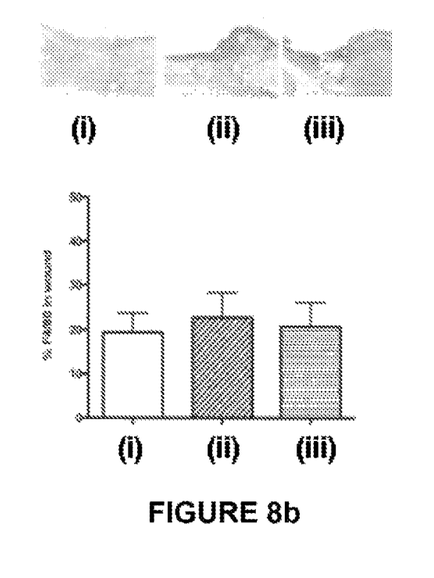

The observed results also include a reduction in apoptosis and an increase in elastin (FIG. 6) during tissue repair.

Overall, the decrease in monocyte chemotactic activity, IL-6 expression and improvements in tissue elasticity and tensile strength indicates that treatment using the selenosugars of the present invention provides a surprising improvement in tissue repair.

While the selenosugars according to the present invention show a surprising improvement in the repair of tissue associated with non-diabetic wounds, they also are remarkably effective for the treatment of diabetic wounds.

Poor tissue repair and non-healing chronic wounds are significant problems for conditions such as metabolic syndrome that includes diabetes. Currently about 15% of people with diabetes will develop a foot ulcer during their lifetime. If the ulcers fail to heal with standard treatment, advanced wound care is employed, including the use of cultured human cells (eg Demagraft, Apligraf) heterogeneic dressings, use of recombinant growth factors (eg Regranex) and hyperbaric oxygen treatment. But these advanced treatments are expensive and are not approved or available in many countries. Even in countries such as Australia where advanced treatment is relatively readily available, 60% of foot amputations are due to the failure of foot ulcers to heal.

Without wishing to be bound by theory, it is believed that diabetes hinders wound healing by its effects on three groups of cells—(i) endothelial cells, (ii) neutrophils and macrophages, and (iii) keratinocytes and fibroblasts—and the parts of the wound healing process with which they are associated.

With reference to endothelial cells observed effects of diabetes on wound healing include:
impaired angiogenesis and neovascularisation
endothelial dysfunction,
diffuse atherosclerotic lesions that decrease blood perfusion,
decreased oxygenation, and
decreased blood flow and decreased endothelial cell proliferation.

With reference to neutrophils and macrophages observed effects of diabetes on wound healing include:
impaired cell migration,
defective macrophage activity
prolonged inflammation, and
build up of the inflammation-associated enzyme myeloperoxidase (MPO) at sites of inflammation.

With reference to keratinocytes and fibroblasts observed effects of diabetes on wound healing include:

impaired cell migration,
increased apoptosis, and
decreased extracellular matrix production.

The data indicate that diabetic mice showed significantly slower wound closure compared to wildtype mice in the absence of treatment using selenosugars according to the present invention. With administration of selenosugars, significant improvements in tissue repair were detected, with wound closure 3-fold better than control db/db mice at day 4 (32% vs 11%, p<0.001) and 2 fold better at day 10 (83% vs 45%, p<0.0001).

Figure 1:
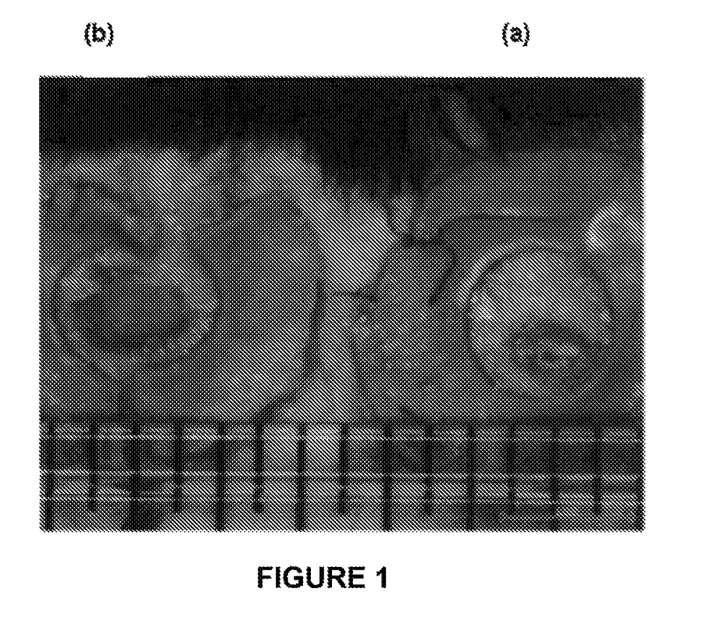
FIG. 1 illustrates wound closure observed in the db/db mouse models topically treated with a 1 mM saline solution of 1,4-anhydro-4-seleno-D-talitol (selenosugar) (b) and a non-selenium control sugar, 1,4-anydro-D-talitol (a).
Figure 2:
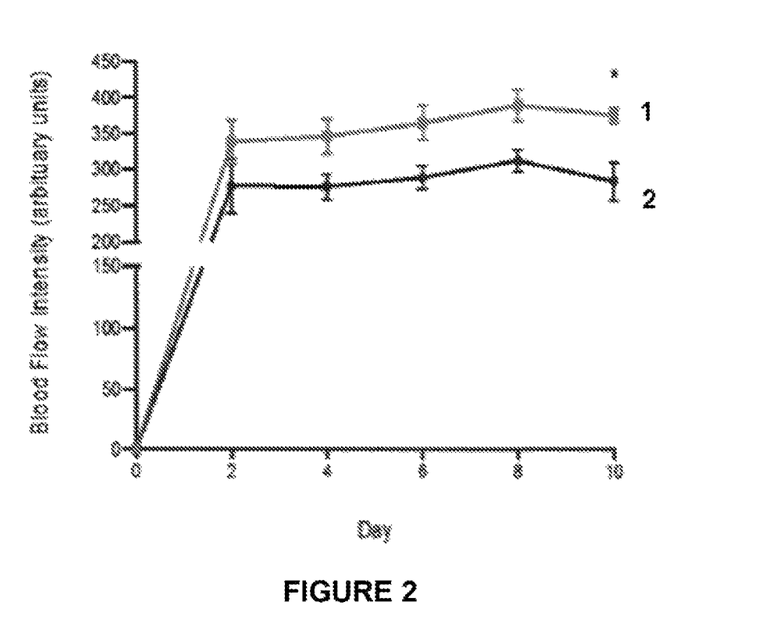
FIG. 2 illustrates vascular perfusion measured by Doppler imaging and corresponding to the selenosugar treated wound (1) and the untreated control wound (2) of the db⁻/db⁻ mouse model of FIG. 1 (where * indicates p, 0.05, and n=6). Doppler imaging is a non-invasive technique used to evaluate blood flow velocity with red blood cells as the moving target.
Figure 3A:
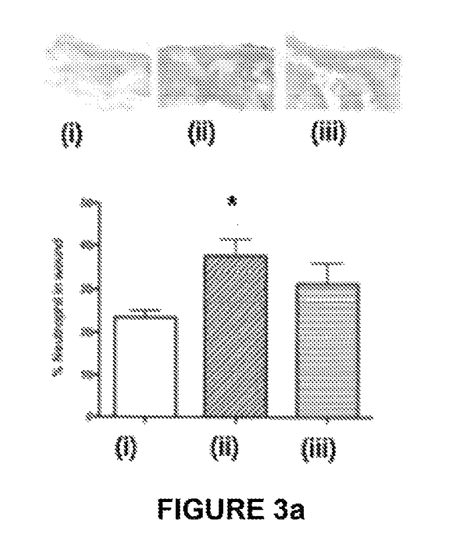
FIGS. 3 to 12 illustrate comparative tissue histology for (a) the wildtype and (b) db/db mouse models, both (i) non-treated mice, (ii) mice treated for 5 days and (iii) mice treated for 10 days. The figures also illustrate plots against time in days for the following wound parameters for (i), (ii) and (iii) (where * indicates p<0.05,  indicates p<0.01, * indicates p<0.001)
Figure 3B:
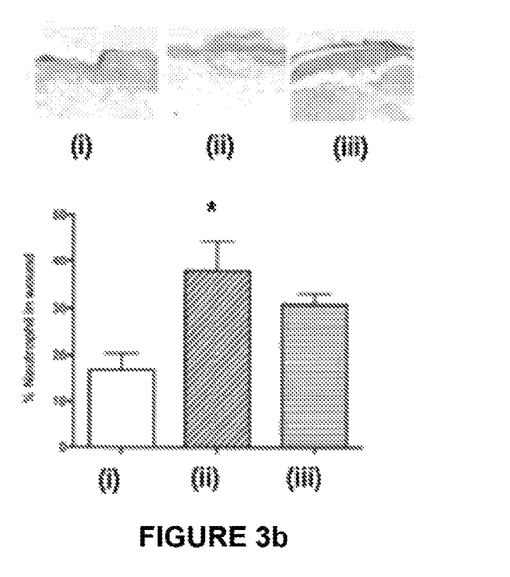

Doppler imaging (FIG. 2) showed improved vascular perfusion (p<0.05) in diabetic but not wildtype mouse, wounds treated with selenosugars of the present invention.

Figure 9A:
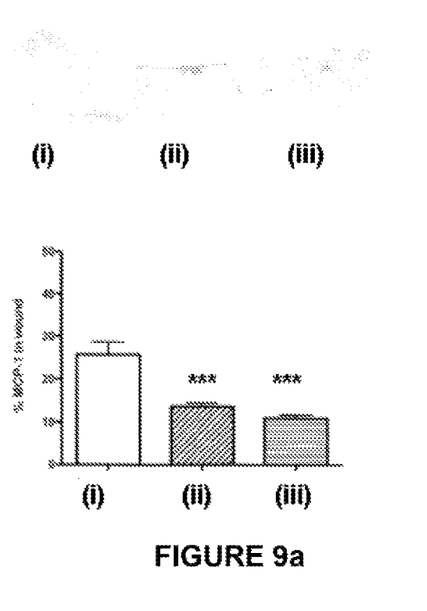
Figure 9B:
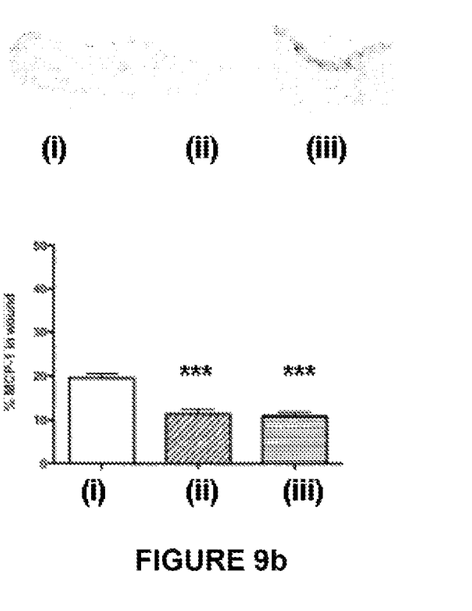
Figure 10A:
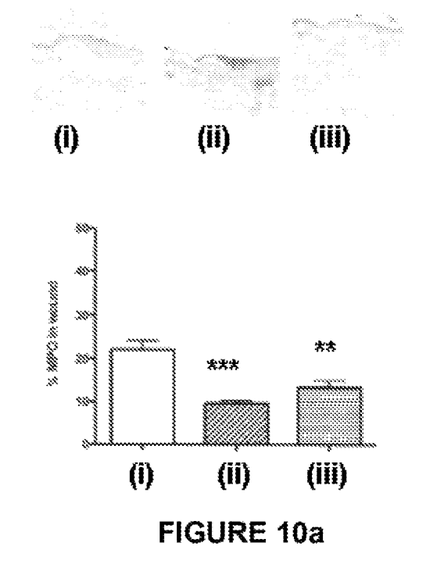
Figure 10B:
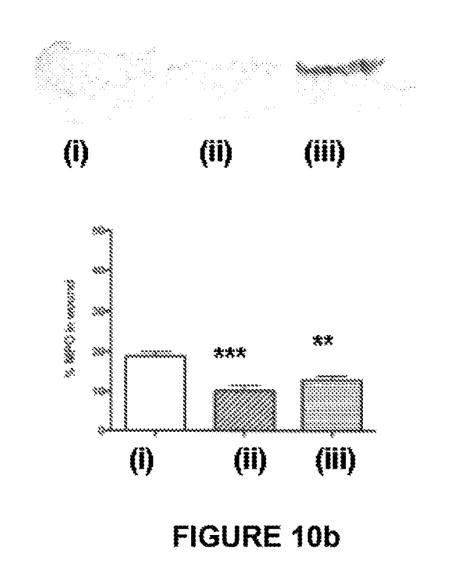
Figure 11A:
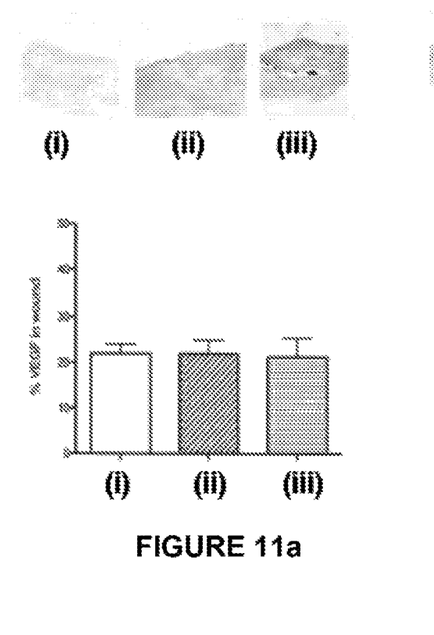
Figure 11B:
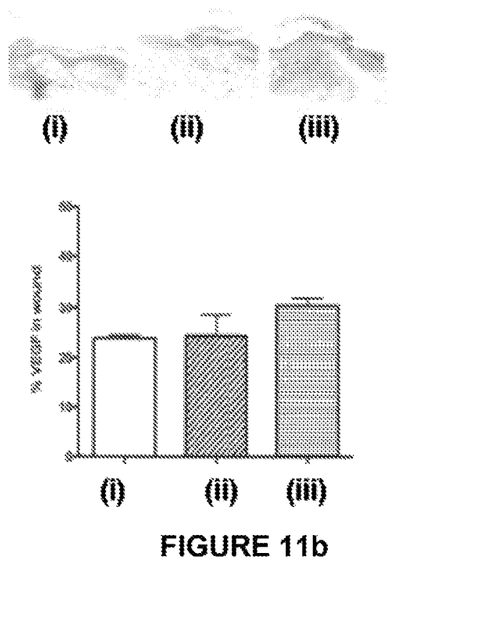
Figure 12A:
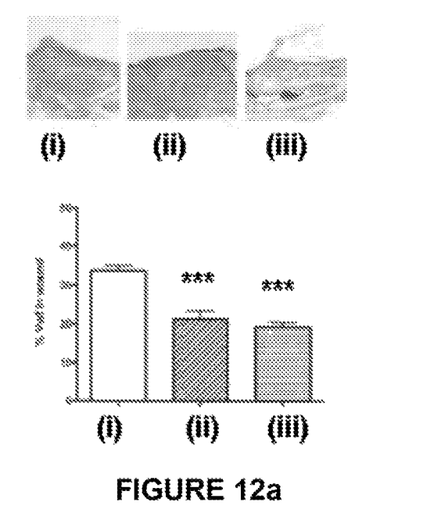
Figure 12B:
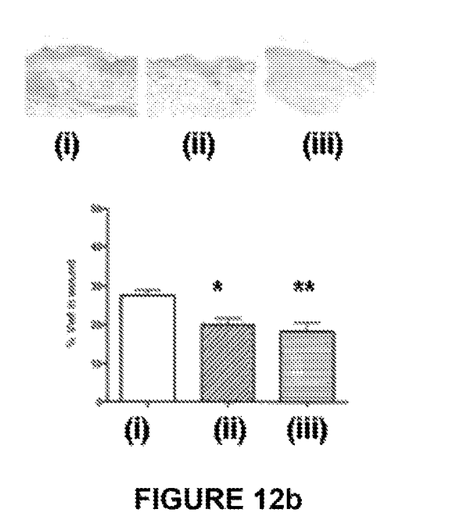
Figure 13A:
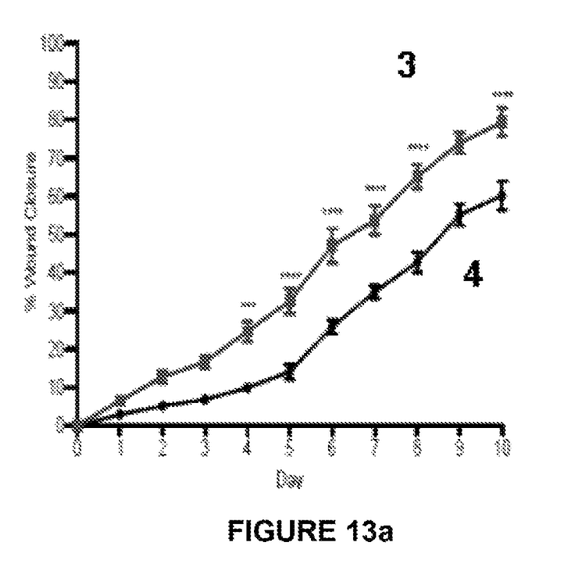
FIG. 13 is a plot illustrating performance of a selenosugar according to the present invention (1,4-anhydro-4-seleno-D-talitol, 1 mM) (3) against performance of a control sugar of identical structure in which the Se is replaced with oxygen (1,4-anyhdro-D-talitol) (4) in wildtype mice (FIG. 13*a*) and in db/db knockout mice (FIG. 13(*b*)) where * indicates p<0.001 and ** indicates p<0.0001 and N=6.
Figure 13B:
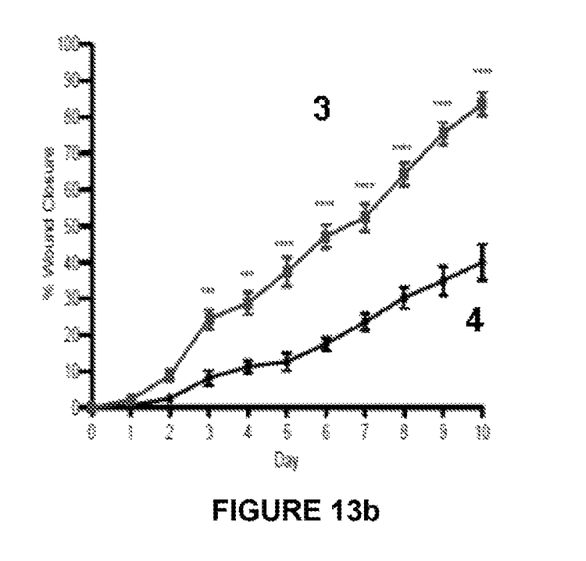

Tissue histology (FIGS. 3 to 12) showed decreased levels of MPO (FIG. 10, p<0.001), MCP-1 (FIG. 9, p<0.001), IL-6 (FIG. 4, p<0.05) and vWF (FIG. 12, p<0.01), and increased elastin levels (FIG. 6, p<0.01) in diabetic wounds treated with selenosugars compared to vehicle.

Comparison with Known Compounds

International patent application WO 2012/054988 (discussed above) discloses the antioxidant properties of a range of selenium-containing cyclic molecules including the preferred compound according to the present invention (Formula II, 1,4-anyhydro-4-seleno-D-talitol, single enantiomer) as well as DL-trans-dihydroxy-1-selenolane (Formula III, racemic) alternatively named trans-3,4-dihydroxytetrahydroselenophene or $DHS_{red}$ as discussed in Chakraborty et al. As discussed above ('Background') $DHS_{red}$ is a known antioxidant and has been shown to accelerate healing of indomethacin-induced stomach ulcers in mice.

Formula (II)

Formula (III)

Figure 15A:
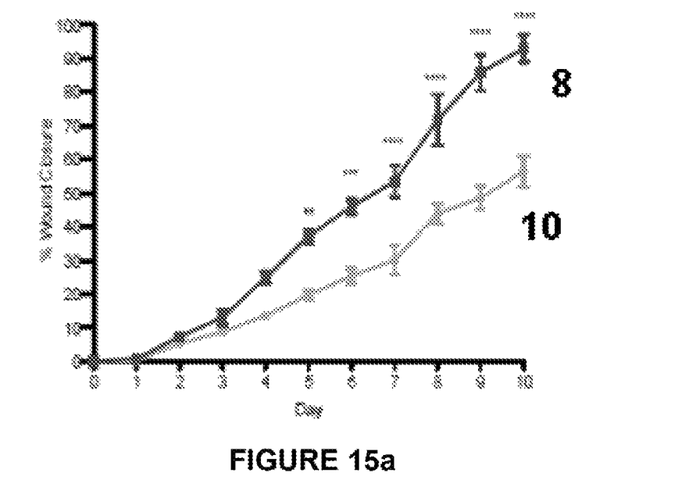
FIG. 15*a* illustrates % wound closure in terms of the wound size and FIG. 15*b* illustrates blood flow intensity (Doppler measurement) in arbitrary units where  indicates p<0.01, * p<0.001 and **** p<0.0001 and N=6.
Figure 15B:
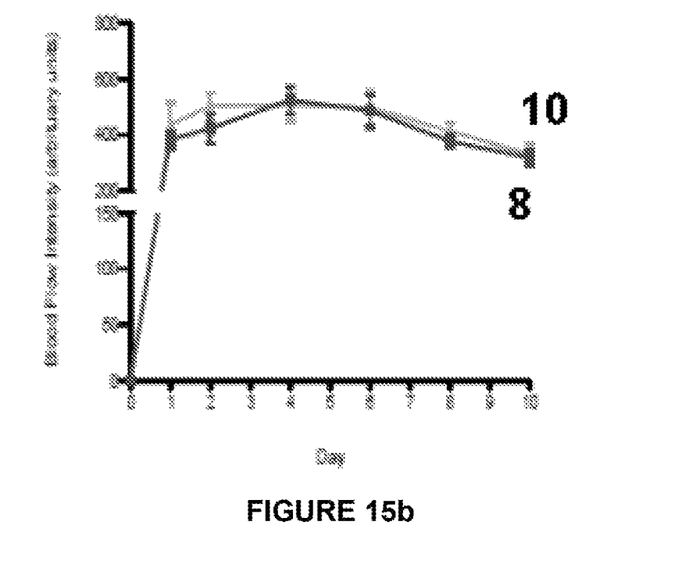

Surprisingly, test result data as illustrated in FIG. 15, have shown that the preferred selenosugar of formula II (8) is superior to formula III (10) in relation to tissue repair during wound healing in wildtype mice. This is not obvious on the basis of the antioxidant capacity of these compounds alone (FIG. 15a).

Figure 16:
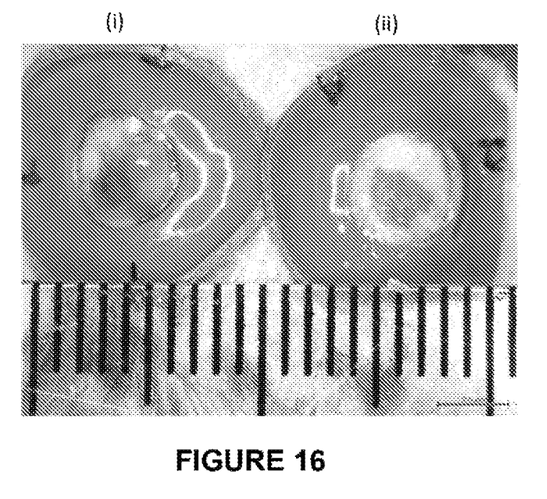
FIG. 16 illustrates a wound treated with a selenosugar according to the present invention (ii) and a wound treated with $DHS_{red}$ (i) at the same dose. Note the development of pus in wound treated with $DHS_{red}$ and the inferior healing.
Figure 17:
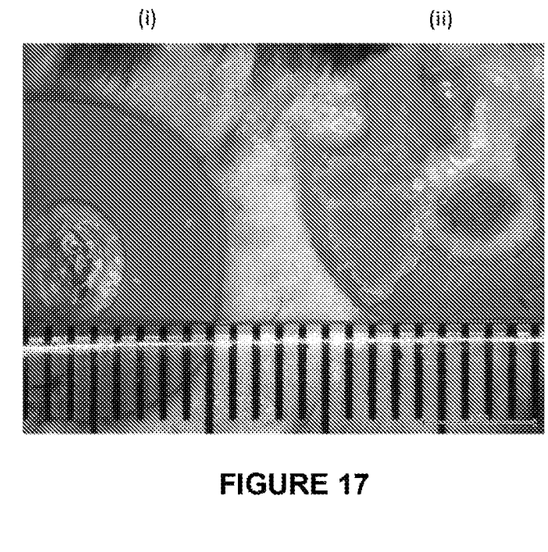
FIG. 17 illustrates typical differences in scar tissue that forms during wound healing in wildtype mice having a wound treated with a selenosugar according to the present invention (ii) and a wound treated with $DHS_{red}$ (i) at the same dose. Note the pronounced scar tissue build up in the wound treated with $DHS_{red}$, while the wound treated with the selenosugar has significantly less scar tissue and is better healed.

FIG. 16 illustrates reduced wound healing with observable pus formation after topical application of DL-trans-3,4,-Dihydroxy-L-selenolane (formula III), while the right image shows improved wound closure and healing by topical application of our lead compound 1. FIG. 16 is a typical image representative of all of the mice in the study.

In addition, the selenosugar of Formula III resulted in an inflammatory response during tissue repair (FIG. 16), while all of the histology would suggest that Formula II triggers an anti-inflammatory response during wound healing. This is also surprising.

Figure 14:
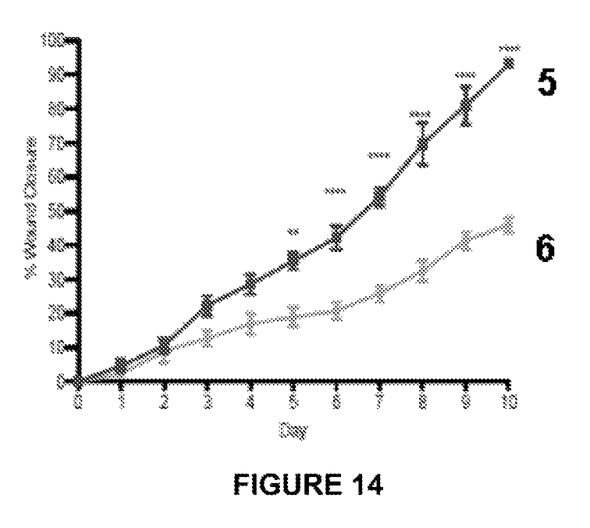
FIG. 14 is a plot illustrating the performance of a selenosugar according to the present invention (1,4-anhydro-4-seleno-D-talitol) (5), against a known antioxidant (6) with similar in vitro antioxidant capacity (selenomethionine) at the same dose in wildtype mice where  indicates p<0.01 and ** indicates p<0.0001 and N=5.

Thus the results illustrate the surprising result that the preferred selenosugars according to the present invention provide superior tissue repair that is not a direct consequence of their antioxidant capacity (FIGS. 14 and 15a). In addition, the seleno compound of Formula III resulted in an inflammatory response during tissue repair (FIG. 16), while all of the histology indicates that selenosugar of Formula II triggers an anti-inflammatory response during tissue repair. This is also surprising as common wisdom in the area would suggest both of these compounds would behave in a similar manner.

Compounds

Where used herein "alkylene" refers to a divalent alkyl group. Examples of such alkylene groups include methylene (—$CH_2$—), ethylene (—$CH_2CH_2$—), and the propylene isomers (e.g., —$CH_2CH_2CH_2$- and —$CH(CH_3)CH_2$—).

"Optionally substituted" in the context of the present invention is taken to mean that a hydrogen atom on the alkylene chain may be replaced with a group selected from hydroxyl, amino, or thio. More-preferably the substituent is hydroxyl.

In a preferred aspect the present invention provides stable, aqueous soluble 5, 6 and 7 membered selenocycles of formula (I) wherein the compound is not metabolisable or derivatisable (to any great extent) by the body.

Preferably, n is 1, 2 or 3. Preferably n is 1 and m is 2, 3 or 4. In another preferred embodiment n is 2 or 3 when m is 2, 3, 4 or 5.

In an embodiment n is 1 or 4, m is 2, 3, or 4 and at least one $R_1$ is (optionally-substituted ($C_1$-$C_3$) alkylene)p-OH where p 1.

In an embodiment n is 1 or 2, m is 2, 3, or 4 and one Rt is (optionally substituted C1-$C_3$ alkylene)p-OH where p=1.

In an embodiment n is 2, m is 4, and one $R_1$ is (optionally substituted $C_1$-$C_3$alkylene)p-OH where p=1.

In the above embodiments preferably the (optionally substituted C1-$C_3$ alkylene)p-OH group is optionally substituted $C_2$-alkylene-OH or $C_1$-alkylene-OH. More preferably the group is —$CH_2OH$.

In the above embodiments where the $C_1$-$C_3$ alkylene group is substituted it is substituted with a hydroxyl group, for example —CH(OH)—$CH_2OH$.

The compounds of the invention may be in crystalline form either as the free compounds or as solvates (e.g. hydrates) and it is intended that both forms are within the scope of the present invention. Methods of solvation are generally known within the art.

It will also be recognised that compounds of the invention may possess asymmetric centres and are therefore capable of existing in more than one stereoisomeric form. The invention thus also relates to compounds in substantially pure isomeric form at one or more asymmetric centres eg., greater than about 90% enantiomeric excess (ee), such as about 95% or 97% ee or greater than 99% ee, as well as mixtures, including racemic mixtures, thereof. Such isomers may be prepared by asymmetric synthesis, for example using chiral intermediates, or mixtures may be resolved by conventional methods, eg., chromatography, or use of a resolving agent.

Alternatively, enantiomerically pure selenosugars of formula (I) may be prepared directly from enantiomerically-pure carbohydrates. In this regard preferred compounds of the present invention may be representative seleno-derivatives of known monosaccharides where the selenium is in the ring position. Examples of suitable selenosugars of this sort may be derived from either D- or L-aldoses such as ribose, arabinose, xylose, lyxose, allose, altrose, glucose, mannose, gulose, idose, galactose, and talose.

The selenosugars of the present invention can be prepared based on the modification of the synthetic procedures described in, for example, M. A. Lucas et al., *Tetrahedron,*

2000, 56:3995-4000, C. Storkey et al., *Chem. Comm.*, 2011, 47, 9693-9695 and C. Storkey et al., *Chem. Res. Toxicol*, 2012, 25, 2589-2599.

During the reactions a number of the moieties may need to be protected. Suitable protecting groups are well known in industry and have been described in many references such as Protecting Groups in Organic Synthesis, Greene T W, Wiley-Interscience, New York, 1981.

Dosage Forms

In another aspect, the present invention provides pharmaceutical compositions for use in wound healing, the composition comprising an effective amount of a selenosugar of the present invention or a pharmaceutically acceptable salt thereof, and optionally a pharmaceutically acceptable carrier or diluent.

The term "composition" is intended to include the formulation of an active ingredient with encapsulating material as carrier, to give a capsule in which the active ingredient (with or without other carrier) is surrounded by carriers.

The pharmaceutical compositions or formulations of the present invention are suitable for topical application, that is, application to internal or external body surfaces such as the skin or mucous membranes. Term is intended to include, for example, application to oral (including buccal and sub-lingual), rectal, nasal or vaginal body surfaces.

The selenosugars of the invention, together with a conventional adjuvant, carrier, or diluent, may thus be placed into the form of pharmaceutical compositions and unit dosages thereof, and in such form may be employed as creams, foams, gels, lotions and ointments, or liquids such as solutions, suspensions, emulsions, elixirs, or capsules.

The selenosugars of the invention, together with any necessary adjuvants may be incorporated into transdermal patches, or wound dressings.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

Formulations containing ten (10) milligrams of active ingredient or, more broadly, 0.1 to one hundred (100) milligrams, per dose, are accordingly suitable representative unit dosage forms although larger doses may also be appropriate, particularly if the area of tissue to be healed is very large.

The compounds of the present invention may be administered to a subject as a pharmaceutically acceptable salt. It will be appreciated however that non-pharmaceutically acceptable salts also fall within the scope of the present invention since these may be useful as intermediates in the preparation of pharmaceutically acceptable salts. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

For preparing pharmaceutical compositions from the compounds of the present invention, pharmaceutically acceptable carriers can be either solid or liquid. A solid carrier can be one or more substances which may also act as diluents, flavouring agents, solubilisers, lubricants, suspending agents, binders, preservatives, tablet disintegrating agents, or an encapsulating material.

For preparing suppositories, a low melting wax, such as an admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomizing spray pump. To improve nasal delivery and retention the compounds according to the invention may be encapsulated with cyclodextrins, or formulated with other agents expected to enhance delivery and retention in the nasal mucosa.

Administration to the surfaces of the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, eg., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component.

The invention also includes the compounds in the absence of carrier where the compounds are in unit dosage form.

The amount of the selenosugar which is to be administered may be in the range from about 10 mg to 2000 mg per day in any convenient unit dose, depending on the activity of the compound and the size and nature of the wound to be treated.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

Various modifications and equivalent arrangements are intended to be included within the spirit and scope of the invention and appended claims. Therefore, the specific embodiments are to be understood to be illustrative of the many ways in which the principles of the present invention may be practiced.

"Comprises/comprising" and "includes/including" when used in this specification is taken to specify the presence of stated features, integers, steps or components but does not preclude the presence or addition of one or more other features, integers, steps, components or groups thereof. Thus, unless the context clearly requires otherwise, throughout the description and the claims, the words 'comprise', 'comprising', 'includes', 'including' and the like are to be construed in an inclusive sense as opposed to an exclusive or exhaustive sense; that is to say, in the sense of "including, but not limited to".

The invention claimed is:

1. A method for skin tissue repair of a patient comprising the step of administering a topical composition to the patient skin tissue in need of repair, wherein said topical composition comprises a selenosugar 1,4-anhydro-4-seleno-D-talitol of formula (II):

2. The method according to claim 1, wherein the patient is diabetic.

3. The method according to claim 1, wherein the patient skin tissue in need of repair is associated with diabetic wounds.

4. The method according to claim 1, wherein the patient skin tissue in need of repair is associated with non-diabetic wounds.

5. The method according to claim 1, wherein said topical composition further comprises an additive selected from pharmaceutically acceptable adjuvants, carriers, diluents and combinations thereof.

6. The method according to claim 1, wherein said topical composition is administered in a dosage form selected from creams, foams, gels, lotions, ointments, liquids, solutions, suspensions, emulsions, elixirs, capsules, transdermal patches, wound dressings and combinations thereof.

* * * * *